US008806378B2

(12) United States Patent
Schwarzberg et al.

(10) Patent No.: US 8,806,378 B2
(45) Date of Patent: Aug. 12, 2014

(54) MOBILE CLIENT APPLICATION FOR MANAGING DISPLAY OF MESSAGES TO USERS

(75) Inventors: Robert Schwarzberg, Boca Raton, FL (US); Timothy J. Dion, Parkland, FL (US)

(73) Assignee: Humana Innovations Enterprises, Inc., Louisville, KY (US)

( * ) Notice: Subject to any disclaimer, the term of this patent is extended or adjusted under 35 U.S.C. 154(b) by 866 days.

(21) Appl. No.: 12/570,694

(22) Filed: Sep. 30, 2009

(65) Prior Publication Data

US 2010/0083280 A1 Apr. 1, 2010

Related U.S. Application Data

(63) Continuation-in-part of application No. 12/117,190, filed on May 8, 2008, now Pat. No. 8,463,618, and a continuation-in-part of application No. 12/264,624, filed on Nov. 4, 2008, now Pat. No. 8,250,477.

(51) Int. Cl.

| | |
|---|---|
| ***G06F 3/048*** | (2013.01) |
| ***G06F 19/00*** | (2011.01) |
| ***G06F 9/54*** | (2006.01) |
| ***G06Q 10/10*** | (2012.01) |
| ***H04M 15/00*** | (2006.01) |
| ***H04W 4/24*** | (2009.01) |

(52) U.S. Cl.

CPC .............. *G06F 19/345* (2013.01); *G06F 9/542* (2013.01); *G06F 3/048* (2013.01); *G06Q 10/109* (2013.01); *H04M 15/00* (2013.01); *H04M 15/68* (2013.01); *H04M 15/83* (2013.01); *H04M 15/835* (2013.01); *H04M 15/84* (2013.01); *H04M 15/844* (2013.01); *H04M 15/85* (2013.01); *H04M 15/851* (2013.01); *H04M 15/852* (2013.01); *H04M 15/854* (2013.01); *H04M 2215/0196* (2013.01); *H04M 2215/81* (2013.01); *H04M 2215/8104* (2013.01); *H04M 2215/8129* (2013.01); *H04M 2215/8137* (2013.01); *H04M 2215/815* (2013.01); *H04M 2215/8158* (2013.01); *H04M 2215/8166* (2013.01); *H04W 4/24* (2013.01); *Y10S 715/963* (2013.01)

USPC ........... 715/844; 709/203; 715/702; 715/716; 715/963; 455/231; 455/412.1; 455/466

(58) Field of Classification Search

CPC ......... G06F 3/048; G06F 9/542; G06F 9/546; G08B 5/00; G08B 5/227; G06Q 10/107; G06Q 10/109; G04G 15/00; G04G 15/006; H04M 1/72566; H04L 12/58; H04L 51/00; H04W 72/00; H04W 72/12; Y10S 379/906

USPC .................. 715/716, 844, 963, 702; 709/203; 455/231, 412.1, 466

See application file for complete search history.

(56) References Cited

U.S. PATENT DOCUMENTS

| | | | | |
|---|---|---|---|---|
| 6,748,450 | B1 * | 6/2004 | Dutta | 709/246 |
| 7,099,659 | B1 * | 8/2006 | Schnake et al. | 455/419 |
| 7,512,420 | B2 | 3/2009 | Lichtenfeld et al. | |
| 2002/0029261 | A1 * | 3/2002 | Shibata | 709/219 |
| 2002/0052957 | A1 * | 5/2002 | Shimada | 709/225 |
| 2003/0117969 | A1 * | 6/2003 | Koo et al. | 370/318 |
| 2003/0125052 | A1 * | 7/2003 | Jou | 455/466 |
| 2003/0194990 | A1 * | 10/2003 | Helferich | 455/412.2 |
| 2005/0003794 | A1 * | 1/2005 | Liu | 455/355 |
| 2005/0013291 | A1 * | 1/2005 | Yamamoto et al. | 370/352 |
| 2005/0288045 | A1 | 12/2005 | Yang et al. | |
| 2006/0224681 | A1 | 10/2006 | Wurster | |
| 2007/0150550 | A1 | 6/2007 | Lin et al. | |
| 2007/0260673 | A1 * | 11/2007 | Shenfield et al. | 709/203 |
| 2008/0013705 | A1 | 1/2008 | Yoffie et al. | |
| 2008/0125165 | A1 | 5/2008 | Park | |
| 2008/0132218 | A1 | 6/2008 | Samson et al. | |
| 2008/0144796 | A1 | 6/2008 | Ringland et al. | |
| 2008/0288604 | A1 | 11/2008 | Major et al. | |
| 2008/0305774 | A1 * | 12/2008 | Ramakrishna | 455/412.1 |
| 2009/0117925 | A1 * | 5/2009 | De Bonis et al. | 455/466 |
| 2009/0135765 | A1 | 5/2009 | Lewis et al. | |
| 2009/0305732 | A1 * | 12/2009 | Marcellino et al. | 455/466 |

2009/0311992 A1* 12/2009 Jagetiya .................... 455/412.1
2009/0328099 A1* 12/2009 Praden et al. .................. 725/39
2010/0042691 A1* 2/2010 Maguire ...................... 709/206

OTHER PUBLICATIONS

Mahmoud, Quasay H., MIDP Database Programming Using RMS: a Persistent Storage for MIDlets, Release 1.0, Dec. 2000, http://developers.sun.com/mobility/midp/articles/persist.

Ortiz, C. Enrique, The MIDP 2.0 Push Registry, Jan. 2003, http://developers.sun.com/mobility/midp/articles/pushreg.

* cited by examiner

*Primary Examiner* — Patrick Riegler
(74) *Attorney, Agent, or Firm* — Standley Law Group LLP

(57) ABSTRACT

A mobile phone messaging system and method for managing display of messages to mobile phone users. A mobile client application operates at user's mobile phone. Mobile content providers manage the display of messages and related interactions throughout a specific period of time (e.g., daily, weekly, bi-weekly). Phone wakeup time data and message identifying data are transmitted from a mobile content provider server to a mobile phone. The wakeup time data and message identifying data are stored in the phone. The wakeup times are also added to a registry at the phone that facilitates launching of applications at the times indicated in the registry. At the specified wakeup times, the mobile client application determines the message identifying data associated with the wakeup time, connects to the mobile content provider server, and provides the message identifying data. The provider responds with a specific message and the mobile client application displays the message.

16 Claims, 1 Drawing Sheet

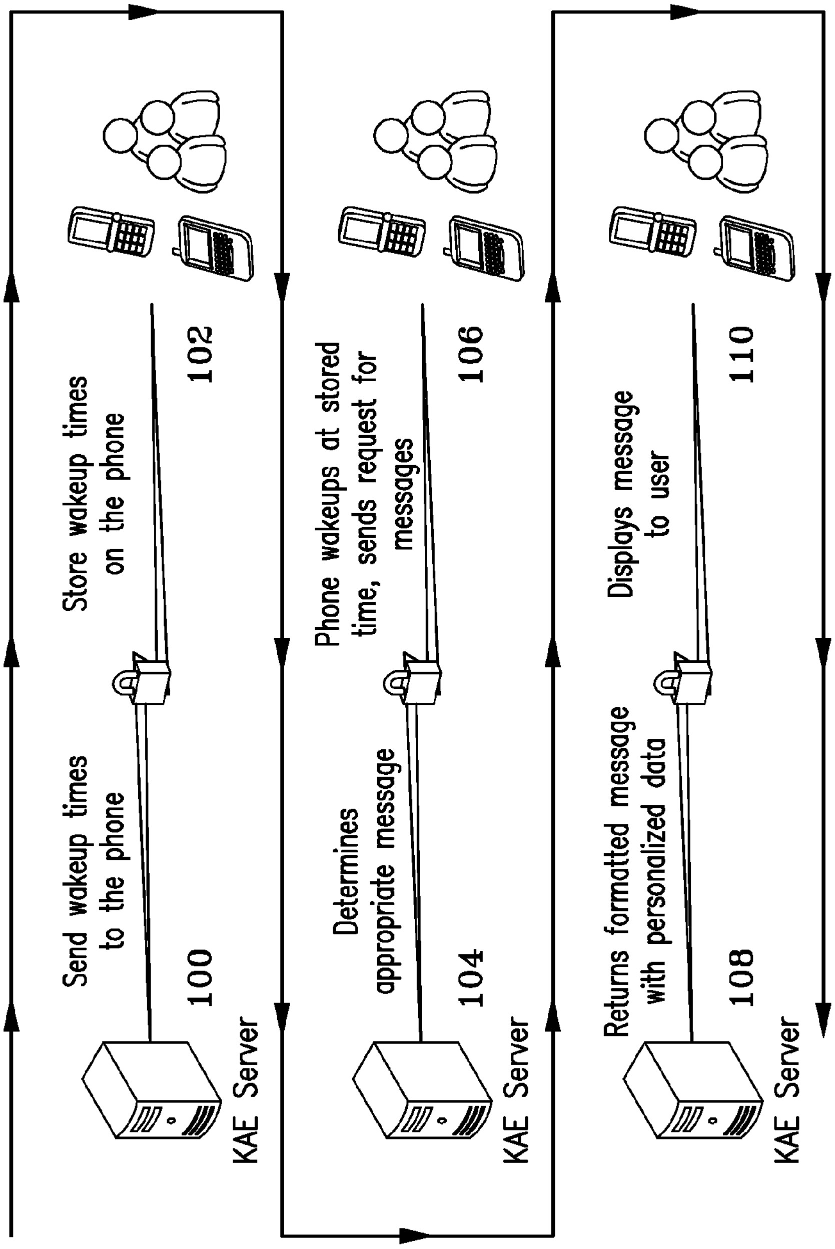
KAE Server
Send wakeup times to the phone
100
Store wakeup times on the phone
102
KAE Server
Determines appropriate message
104
Phone wakeups at stored time, sends request for messages
106
KAE Server
Returns formatted message with personalized data
108
Displays message to user
110

MOBILE CLIENT APPLICATION FOR MANAGING DISPLAY OF MESSAGES TO USERS

CROSS-REFERENCE TO RELATED APPLICATIONS

This application is a continuation-in-part of U.S. patent application Ser. No. 12/117,190 filed May 8, 2008, titled METHOD FOR TAILORING STRATEGY MESSAGES FROM AN EXPERT SYSTEM TO ENHANCE SUCCESS WITH MODIFICATIONS TO HEALTH BEHAVIORS, which is incorporated herein by reference, and a continuation-in-part of U.S. patent application Ser. No. 12/264,624, filed Nov. 4, 2008, titled MOBILE CLIENT APPLICATION FOR MANAGING USER INTERFACE COMPONENTS, which is incorporated herein by reference.

TECHNICAL FIELD

The present invention relates generally to mobile device client applications. In particular, the present invention is a mobile device client application for managing the display of messages that are received from a mobile content provider according to display times associated with the messages.

BACKGROUND OF THE INVENTION

As mobile computing services as well as powerful mobile computing devices have proliferated, people increasingly view their cell phones and other mobile devices as their communication medium of choice. Mobile based services are wide ranging and include not only basic telecommunications and text messaging services but also web browsing and information retrieval, games, music, and even movie and television viewing. Although mobile phones may be used for personal activities such as maintaining contact with family and friends as well as for recreational activities such as listening to music and playing games, people also rely on them for important business and emergency communications. As a result, many mobile phone users make certain their phones are always available and always on. The portability of the mobile phone coupled with the variety of features and functionality that are supported have caused many people to choose mobile devices and services over traditional desktop devices and wire services for all kinds of communications.

Because mobile phones are the preferred method of communication for many people, they are using them to receive more and more text-based communications in addition to phone calls and audio messages. To respond to the preference of mobile phone users to receive all communications by phone, mobile content providers are developing applications for transmitting messages that conform to various current messaging standards. One messaging protocol that is commonly used is the Short Message Service (SMS) protocol. The protocol supports transmission of text only messages of a limited size. Messages are transmitted through message centers or gateways and held for delivery to recipients. Typically, users select a messaging icon to access the messages. While most messages are successfully delivered, there are limits associated with the use of SMS protocol for text messaging. There are limits on the size of the messages and sending and responding to such messages requires mobile phone users to use the numeric keypad to enter text. The process of drafting a message is time consuming and error-prone. As a result, many people use shorthand and acronyms that save time but are not necessarily understood or decipherable by the recipient. In addition, a per message cost is typically charged to the sender and the recipient for every SMS message that is transmitted to a mobile phone.

An alternative to SMS protocol for text messaging is the use of the Wireless Application Protocol (WAP). Use of the protocol requires users to install a special WAP browser on their mobile phones. WAP is typically used for transmission of email messages and for access to websites. When accessing websites, data from the site is converted to Wireless Markup Language (WML) and accessed via the WAP browser. Although WAP supports graphics in addition to text, it effectively requires the provider to customize content for delivery to mobile phones and does not support all of the features and functionality of HTML. For many mobile content providers, its appeal as a communications platform is limited because development and maintenance of WAP applications is costly and the protocol has limited features and functionality.

While the use of SMS protocol and WAP are adequate for many applications, they do not provide much more than basic functionality for receiving and delivering messages. As mobile content providers vie for the attention of mobile phone users, they want to be sure that their messages are not only delivered but viewed as well. One way to be sure that a message is viewed is to ask the recipient for confirmation that the message was received and viewed. Because interaction using SMS protocol requires use of the numeric keypad as a typewriter, providing such confirmation is cumbersome. The content of the return message depends upon what the user types and therefore, in some cases, the user's response may not be recognized by the provider's application. From the content provider's standpoint, the message is never acknowledged even though the user may have viewed it.

The use of WAP facilitates more interaction between the mobile phone user and content provider due to the use of graphics that can provide interactivity. Limitations related to use of WML, however, can compromise the interactivity because all of the content must be customized for use in a mobile environment. The standard is specific to mobile devices and therefore, development and maintenance of applications can be costly to a developer.

Even if SMS protocol and WAP are adequate for a mobile content provider's needs, they provide only functionality for delivering messages or content. The protocols are not designed for message management. If the mobile phone is off or unavailable, the messages are not delivered. The message centers or gateways that support the protocols may provide some delivery support and continue trying to deliver a certain message until a specified number of failures occur. Additional support is not provided. In particular, the phone does not have information or data from the mobile content provider that the provider might be trying to deliver a message.

Effective messaging for mobile content providers often involves not only knowing that messages were delivered to and viewed by users but also knowing that the recipients viewed them in a timely manner. For important or urgent communications, mobile content providers would like acknowledgment from their users that a particular message was viewed during a particular timeframe. Although the mobile phone itself can provide some feedback in this regard, in many instances, an explicit acknowledgment from the user is the only way to know that a message was actually communicated to the user. Furthermore, in some instances, the mobile content provider may want the mobile phone user to provide more than an acknowledgment of receipt. In some cases, the mobile content provider may want to know the mobile phone user's response to a particular query. In such instances, the ability to respond with more than a "yes" or "no" answer is important. Therefore, the ability for mobile content providers and mobile phone users to interact in a particular way is important.

There is a need for mobile phone messaging technology that facilitates mobile phone user and mobile content provider interaction. There is a need for a mobile phone messaging system and method that supports highly interactive communications between mobile content providers and mobile phone users. There is a need for a mobile phone messaging system and method that supports graphic-based as well as text-based communication so that users can respond easily to messages provided by mobile content providers. There is a need for a mobile phone messaging system and method that allows mobile content providers to manage timely display of messages and user reactions to messages.

SUMMARY OF THE INVENTIVE CONCEPT

The present invention a mobile phone messaging system and method for managing display of messages to mobile phone users. A mobile client application that operates at user's mobile phone supports graphic intensive content and is device independent so that it can operate on a variety of different mobile devices. Mobile content providers that communicate frequently with their mobile phone users can use the system and method to manage the display of messages and related interactions throughout a specific period of time (e.g., daily, weekly, bi-weekly). The number of messages that are provided during a time period, the times that the messages are displayed during the time period, and the message content are configurable. Messages are scheduled for display at the users' mobile devices and interactions with the mobile content provider's server are managed through the mobile client application so that the appropriate messages are communicated to the users at the appropriate times. The mobile client application and mobile content provider communicate using the system and method of message display management so that messages are provided in a timely manner.

In an example embodiment of the present invention, a mobile client application with messaging features and functionality is loaded on a user's mobile phone. Phone wakeup time data and message content or context data are transmitted from a mobile content provider server to a user's mobile phone for use by the mobile client application. The wakeup time data and message content or context data are stored in the mobile phone and remain at the phone, even if the user turns off the phone. The wakeup times are also added to a registry at the phone that facilitates launching of applications on the phone at the times indicated in the registry. The registry is monitored using features and functionality of the mobile device and the phone launches the mobile client application at the times specified in the registry. The mobile client application then determines the message content or context associated with the wakeup time and connects to the mobile content provider server to request the specific message to be displayed on the mobile phone. If the message prompts the mobile phone user to respond, the user's response is transmitted from the mobile phone to the mobile content provider server.

BRIEF DESCRIPTION OF THE DRAWINGS

FIG. 1 is a flow diagram of a message display management system and method for an example embodiment of the present invention.

DETAILED DESCRIPTION

Referring to FIG. 1, a flow diagram of a message display management system and method for an example embodiment of the present invention is shown. An application at a mobile content provider server determines phone wakeup times for delivering a plurality of messages to a user's mobile phone 100. The number of messages and the times for displaying the messages at the phone vary according to the mobile content provider's needs. Associated with each message time is a message identifying data for determining the specific content of a message to be transmitted from the mobile content server to the user's mobile phone at the specified time. The identifier may identify a specific message in a database at the server or provide a context for a message to be generated at the server and then transmitted to the user's mobile phone. The wakeup times and message identifying data are transmitted to the mobile phone and stored there by a mobile client application that receives data from the mobile content provider 102.

In an example embodiment of the present invention, HTTP, HTML, XML, and Java are used to implement the features and functionality of the mobile client application. In an example embodiment of the present invention, the phone "push registry" of the Java Application Management System (AMS) is used to hold the phone wakeup times. The push registry is essentially a lookup table on a mobile device to manage "push-enabled" applications. The push registry allows applications called "MIDlets" to configure themselves to be launched automatically according to a timer-based alarm. Timer-based activation features in the push registry may be used to schedule times for launching a MIDlet to synchronize with the server periodically and then sleep. The push registry launches a MIDlet when it determines that the mobile phone time matches a time for an event (MIDlet launch) registered in the push registry. MIDlets may also be registered for push events that are activated using inbound connections.

In an example embodiment, the mobile client application stores the phone wakeup times and associated message identifying data in the phone's Record Management Storage (RMS) database. The RMS is a persistent storage area for use by MIDlets that execute on a phone. In the example embodiment, the entries in the RMS include the name of the MIDlet as well as an assigned port number for establishing a connection with the server. The MIDlet may be programmed to retrieve data from the RMS as needed.

The mobile client application also adds the wakeup times to the mobile phone application registry. When the MIDlet is not active, the push registry handles any push events that occur by activating the appropriate MIDlet to handle them. For each alarm, the push registry knows which MIDlet to activate as each MIDlet is registered on a different port. When the push registry determines that the mobile phone time matches a time for an event (launch MIDlet) in the push registry, the mobile client application uses the wakeup message time to find the associated message identifying data in the RMS database. The mobile client application then sends a request to the mobile content provider server to get the appropriate message using the message identifying data 104. The mobile content provider server determines the appropriate message (e.g., using the message identifying data to find it in a database or to generate it) 106 and returns the message 108 for the mobile client application to display to the user 110. A system and method for receiving and displaying content as well as interactive components on a mobile device display is described in U.S. patent application Ser. No. 12/264,624, entitled "Mobile Client Application for Managing User Interface Components."

The mobile client application interactions with the server based expert system facilitate the display of appropriate messages at appropriate times. The mobile client application, on every request to the server, constantly refreshes its list of wakeup times. These times are determined by the server with respect to the content provider's rules and definitions. This constant refresh cycle ensures that a user receives messages at appropriate times.

Timing of the messages is determined by the server including appropriateness relative to time zone. One of the parameters sent during a server request is the time from the phone (in milliseconds) so that appropriate time offsets can be determined by the server and the message content is delivered at the correct time. Storing time delivery information on the phone also allows for a more stable, guaranteed delivery approach. Use of the push registry accomplishes this by polling against the current phone time and the time stored in the registry. This polling approach ensures that even if a message was missed because the phone was off or out of network coverage, the next scheduled message will be delivered when the phone is once again available.

Another benefit to the disclosed mobile client application and server communications is that the server can document user interactions. In an example embodiment, the mobile client application captures program, module, page, and action events. This information may be transferred from the phone to the server and stored on the server for future analysis. The analysis conducted against this type of information provides for real time system adjustments based on user behavior. Message content and/or message may be modified depending upon the user's reaction to various messages.

With the present invention, phone wakeup times for displaying messages to users can be determined and transmitted in "batches" for use during a particular time period (e.g., daily, weekly, bi-weekly, etc.) The number of message identifiers and the specific wakeup times that a mobile content provider transmits depends upon the type of content that is provided to the user and the type of interactions that are supported. For example, in a system for providing strategy messages to mobile phone users to promote health behavior modifications as described in U.S. patent application Ser. No. 12/117,190, entitled "Method for Tailoring Strategy Message from an Expert System to Enhance Success with Modifications to Health Behaviors," a user of the system may define a daily schedule of activities and meal preferences. Based on the personal data and preferences provided to the mobile content provider, a server application determines when activity and meal messages should be displayed to users to remind them to perform certain tasks and to elicit feedback regarding performance of the tasks. In an example schedule, a user may take a weight reading at 7:00 AM, eat a suggested breakfast at 7:30 AM, complete a suggested physical activity at 8:00 AM, and eat a suggested lunch and dinner at the specified times. The mobile client application of the present invention may be used to establish daily phone contacts with the mobile content provider according to the user's schedule.

A set of phone wakeup times and messages is created for user at the server based on the schedule data. The phone wakeup times and message identifying data are sent from the mobile content provider to the mobile phone for use by the mobile client application. Throughout the day, a variety of tailored daily messages are displayed to the user according to the phone wakeup times in the registry. A first message relates to the 7:00 AM weight reading, a second message relates to the 7:30 AM breakfast, a third message relates to the 8:00 AM physical activity, a fourth message relates to the time for lunch, and a fifth message relates to the time for dinner. The tailored messages are pushed from the computer based expert system to the user's cell phone at the specified times.

Every day, each user of the system may be provided with a new schedule of messages that include "Meal Wake-up" messages, "Fitness Wake-up" messages, a "Goal Reminder/Tip of the Day Wake-up" message, a "Strategy Reminder Wake-up" message, and a "Snack Tally" message. To promote behavior modifications, the daily tailored messages may arrive at the mobile phone within a certain time period based on the user's specified times for various activities rather than at the same time every day. For example, an individual user may receive a meal wakeup message any time from 15 to 45 minutes before the user's preferred time for each daily meal. Because the actual time that the messages are displayed varies from day-to-day, the user is more likely to respond to the messages. The time of display will not become so predictable that the user is tempted to ignore the message. If the time of display varies, the user is unlikely to know whether the phone wakeup occurs because of a message from the mobile content provider or for another reason. As a result, the user is more likely to look at the display. By frequently reviewing and responding to messages related to health behaviors, the user is more likely to complete the suggested activities or tasks and therefore, to modify his or her behaviors.

In another example embodiment of the present invention, a financial institution may use the message display management features and functionality to provide account information and reminders to customers of the institution. The phone wakeup times and message identifying data may be provided weekly or bi-weekly rather than daily. The message content may comprise current account balances that may serve as reminders that a balance should be increased for various reasons. The message content may further comprise reminders to make a mortgage payment or to pay other bills. The messages may be sent a week or several days in advance of the payment due dates. In addition, reminders may be sent until the user acknowledges that the payment has been made. The use of appropriately timed financial account and payment messages may be used to modify the mobile phone user's financial behavior just as a meal and activity messages may be used to modify the mobile phone user's health behaviors.

It will be recognized by those of skill in the art that various modifications, alternative implementations, and equivalents may be used without departing from the spirit of the invention. For example, the number of phone wakeup times and message identifiers that are transmitted in a batch may vary according to the mobile content provider's needs. The manner in which message content is determined may also vary. Finally, the messages may relate to a variety of areas such as health, finances, etc. Accordingly, the above description does not limit the scope of the invention, which is defined in the following claims.

The invention claimed is:

1. A computerized system for managing display of messages on mobile device comprising:

a server that:

(a) determines a plurality of phone wakeup times for displaying messages during a specified period of time;

(b) associates message identifying data with each of said plurality of phone wakeup times;

(c) transmits said phone wakeup times and message identifying data to a mobile device;

(d) at said phone wakeup times for said specified period of time, receives from a mobile client application at said mobile device said message identifying data associated with said phone wakeup times;

(e) determines specific message content using said message identifying data received from said mobile client application; and a mobile device that:

(a) receives said phone wakeup times and message identifying data from said server;

(b) adds said phone wakeup times to a registry at said mobile device;

(c) stores said phone wakeup times and said message identifying data in a record storage area of said mobile phone;

(d) in response to a phone wakeup event in said registry, launches a mobile client application that:

(1) uses a wakeup time associated with said wakeup event to locate associated message identifying data in said record storage area; and (2) transmits to said server said message identifying data for said phone wakeup event;

(e) receives from said server specific message content determined by said server using said message identifying data; and (f) displays at said mobile device said specific message content.

2. The computerized system of claim 1 further comprising a database of messages associated with said message identifying data.

3. The computerized system of claim 1 wherein said server determines specific message content using said message identifying data by generating a message using said message identifying data.

4. The computerized system of claim 1 wherein said specific message content is selected from the group consisting of health-related messages and finance-related messages.

5. The computerized system of claim 4 wherein said health-related messages comprise reminders to eat a meal.

6. The computerized system of claim 4 wherein said finance-related messages comprises reminders to pay a bill.

7. The computerized system of claim 1 wherein said specified period of time is selected from the group consisting of a daily, weekly, and bi-weekly.

8. The computerized system of claim 1 wherein said server updates said phone wakeup times after said specified period of time.

9. A computerized method for managing display of messages on mobile device comprising:

(a) determining at a server a plurality of phone wakeup times for displaying messages during a specified period of time;

(b) associating at said server message identifying data with each of said plurality of phone wakeup times;

(c) transmitting from said server to a mobile device said phone wakeup times and message identifying data;

(d) receiving at said server from said mobile device in response to a phone wakeup event at said mobile device said message identifying data associated with said phone wakeup time, said message identifying data:

(1) retrieved from a record storage area in said mobile device by a mobile application launched at said phone wakeup time; and (2) located in said record storage area according to said phone wakeup time associated with said message identifying data;

(e) determining at said server specific message content using said message identifying data received from said mobile device; and (f) transmitting for display at said mobile device said specific message content.

10. The computerized method of claim 9 wherein determining at said server specific message content comprises using said message identifying data to locate a message in a database.

11. The computerized method of claim 9 wherein determining at said server specific message content comprises using said message identifying data to generate a message.

12. The computerized method of claim 9 wherein said specific message content is selected from the group consisting of health-related messages and finance-related messages.

13. The computerized method of claim 12 wherein said health-related messages comprise reminders to eat a meal.

14. The computerized method of claim 12 wherein said finance-related messages comprises reminders to pay a bill.

15. The computerized method of claim 9 wherein said specified period of time is selected from the group consisting of a daily, weekly, and bi-weekly.

16. The computerized method of claim 9 wherein said server updates said phone wakeup times after said specified period of time.

* * * * *